US012672955B2

(12) United States Patent
Snyder

(10) Patent No.: US 12,672,955 B2
(45) Date of Patent: Jul. 7, 2026

(54) OPHTHALMIC PROSTHETIC TO TREAT NEGATIVE AND POSITIVE DYSPHOTOPSIA

(71) Applicant: Michael Snyder, Cincinnati, OH (US)

(72) Inventor: Michael Snyder, Cincinnati, OH (US)

( * ) Notice: Subject to any disclaimer, the term of this patent is extended or adjusted under 35 U.S.C. 154(b) by 0 days.

(21) Appl. No.: 17/405,741

(22) Filed: Aug. 18, 2021

(65) Prior Publication Data

US 2023/0054347 A1 Feb. 23, 2023

(51) Int. Cl.
*A61F 2/16* (2006.01)

(52) U.S. Cl.
CPC .. *A61F 2/1608* (2015.04); *A61F 2002/16901* (2015.04); *A61F 2002/16905* (2015.04); *A61F 2002/1696* (2015.04)

(58) Field of Classification Search
CPC .......... A61F 2/1608; A61F 2002/16901; A61F 2002/16905; A61F 2002/1696; A61F 2/1451; A61F 2/15; A61F 2/1613
See application file for complete search history.

(56) References Cited

U.S. PATENT DOCUMENTS

| | | | |
|---|---|---|---|
| 4,634,442 A | 1/1987 | Link | |
| 5,192,319 A | 3/1993 | Worst | |
| 5,290,892 A * | 3/1994 | Namdaran | A61F 2/1616 |
| | | | 526/289 |
| 5,662,706 A | 9/1997 | Legerton et al. | |
| 6,106,553 A | 8/2000 | Feingold | |
| 6,228,115 B1 | 5/2001 | Hoffmann et al. | |

| | | | |
|---|---|---|---|
| 7,217,289 B2 | 5/2007 | Coronco | |
| 7,455,691 B2 | 11/2008 | Feingold et al. | |
| 8,652,206 B2 | 2/2014 | Masket | |
| 9,433,498 B2 | 9/2016 | Masket | |
| 9,770,325 B2 | 9/2017 | Zhao | |
| 10,765,508 B2 | 9/2020 | Vilupuru et al. | |
| 10,869,752 B2 | 12/2020 | Christie et al. | |
| 10,925,721 B2 | 2/2021 | Roop | |
| 2005/0143812 A1 | 6/2005 | Paul et al. | |
| 2008/0269891 A1 | 10/2008 | Hong et al. | |
| 2009/0222087 A1* | 9/2009 | Coroneo | A61F 2/1694 |
| | | | 623/6.43 |

(Continued)

FOREIGN PATENT DOCUMENTS

| | | |
|---|---|---|
| WO | 2013/082545 A1 | 6/2013 |
| WO | 2013/123265 A1 | 8/2013 |

(Continued)

OTHER PUBLICATIONS

Definition of dysphotopsia retrieved from: https://www.aao.org/eyenet/academy-live/detail/managing-dysphotopsia (Year: 2023).*

(Continued)

*Primary Examiner* — Megan Y Wolf

(74) *Attorney, Agent, or Firm* — The Dobrosin Law Firm, P.C.

(57) ABSTRACT

An ophthalmic prosthetic and method for correcting negative and positive dysphotopsia. The ophthalmic prosthetic comprises a peripheral light blocking implant member adapted to locate in a gap between an iris and an intraocular implant lens. The gap is between the anterior surface of the lens and the posterior portion of the iris. An opacity of the peripheral light blocking implant member is selectively positioned to block passage of light.

11 Claims, 5 Drawing Sheets

(56) References Cited

U.S. PATENT DOCUMENTS

| | | | | |
|---|---|---|---|---|
| 2010/0057202 | A1 | 3/2010 | Bogaert | |
| 2013/0053953 | A1 | 2/2013 | Silvestrini | |
| 2013/0204364 | A1* | 8/2013 | Olson | A61F 2/1648 |
| | | | | 623/6.34 |
| 2013/0238091 | A1 | 9/2013 | Danta et al. | |
| 2014/0379078 | A1 | 12/2014 | Trindade | |
| 2015/0342725 | A1* | 12/2015 | Cuevas | A61F 2/1601 |
| | | | | 623/6.16 |
| 2016/0135947 | A1* | 5/2016 | Webb | A61F 2/15 |
| | | | | 623/6.17 |
| 2020/0197164 | A1* | 6/2020 | Das | G02C 7/02 |
| 2021/0015604 | A1* | 1/2021 | Ma | A61F 2/1635 |
| 2022/0110739 | A1* | 4/2022 | Wortz | A61F 2/0077 |
| 2023/0116694 | A1* | 4/2023 | Ho | A61F 2/1618 |
| | | | | 623/6.17 |

FOREIGN PATENT DOCUMENTS

| | | | |
|---|---|---|---|
| WO | 2017/091520 | A1 | 6/2017 |
| WO | 2020/065412 | A1 | 4/2020 |

OTHER PUBLICATIONS

Duke Health Standard Cataract Surgery video obtained from https://www.youtube.com/watch?v=JUhM6LMkjBk (Year: 2024).*

Peter Choyce, Intra-ocular Lenses and Implants, H.K. Lewis & Co. LTD, p. 24-26 (1964).

Lewandowska et al., The technique of measurement of intraocular lens surface roughness using Atomic Force Microscopy, Interdisciplinary Journal of Engineering Sciences, vol. II, No. 1 (2014).

International Search Report and Written Opinion, PCT Application No. PCT/US2022/040287 dated Dec. 5, 2022.

International Search Report and Written Opinion, PCT Application No. PCT/US2022/040315 dated Dec. 1, 2022.

Modesti et al., "Preoperative and postoperative size and movements of the lens capsular bag: Ultrasound biomicroscopy analysis"; J Cataract Refract Surg, vol. 37: 1775-1784, Oct. 2011.

Holladay et al., Negative dysphotopsia: Causes and rationale for prevention and treatment; Laboratory Science vol. 43 Issue 2, pp. 263-275, Feb. 2017.

Prakhyat Roop, MBBS, The Ring of Light, AAO 2019 Video Program (Mar. 26, 2020) available online at http://www.aao.org/education/annual-meeting-video/ring-of-light.

* cited by examiner

OPHTHALMIC PROSTHETIC TO TREAT NEGATIVE AND POSITIVE DYSPHOTOPSIA

FIELD

The present teachings generally relate to an ophthalmic prosthetic and a method for correcting negative and/or positive dysphotopsia. The ophthalmic prosthetic may create a barrier to oblique light striking or bypassing the anterior edge of an intraocular implant lens. This barrier may be effective by masking at least a portion of an anterior edge of an intraocular implant lens and/or masking an aphakic space peripheral to an anterior edge of an intraocular implant lens, or by filling a gap located between a posterior surface of an iris and an anterior portion of an intraocular implant lens, thereby preventing light from entering the space peripheral to the intraocular implant lens.

BACKGROUND

Aphakia is an ophthalmic condition whereby a natural lens is absent from the eye. Aphakia can result from removal of the natural lens during cataract surgery, genetic disorders causing birth without a natural lens, or dislocation of a natural lens by an injury and/or genetic susceptibility to dislocation of a natural lens. Aphakia is typically associated with an impairment in the ability to focus on objects that the afflicted is viewing. For example, the afflicted may exhibit long sightedness, whereby focusing on both near and far objects is difficult. As another example, the afflicted may exhibit loss of accommodation, whereby focusing on objects that are moving nearer or further away from the eye is difficult.

Aphakia can be treated by surgical implantation of an intraocular implant lens. In a phakic eye, the intact natural crystalline lens, otherwise referred to as a natural lens herein, has a convex anterior contour and the pupil glides along the anterior contoured surface as it expands or contracts. In a pseudophakia eye, the prosthetic intraocular lens is thinner and has a lesser anterior convexity relative to a natural crystalline lens. The anterior surface of the prosthetic intraocular lens thereby rests more posteriorly in the eye than that of the natural lens. This pseudophakic anatomy results in a gap between the posterior surface of the iris and the anterior surface of the intraocular implant lens after cataract surgery. In other words, the lesser thickness and positioning of the intraocular implant lens relative to the natural lens gives rise to the gap. Light entering the eye along a path that is oblique (e.g., tangential) to the intraocular implant lens can pass through this gap, particularly in a physiologically temporal region. Some of this light may strike the edge of the lens and be refracted posteriorly toward the retina, while other light rays may be un-refracted and may strike the nasal retina more anteriorly than the refracted light rays. As a result, patients can have a dark area in their vision. Some patients report of the dark area being crescent-shaped or line-shaped, although other shapes may be possible. This condition is conventionally referred to as negative dysphotopsia. Other patients may notice the anteriorly striking rays more and will report a bright arc or line in the physiologically temporal periphery of their visual field. Some intraocular implant lenses have an edge shaped like a base-out prism, which can accentuate the appearance of a bright line or arc.

In addition to intraocular implant lens positioning within the eye, negative dysphotopsia has conventionally been associated with other ophthalmic conditions such as ring scotoma, enigmatic penumbra, temporal corneal incision, displacement and/or magnification of a blind spot, and transversal propagation of light reflected internally within a lens. Some solutions to these other ophthalmic conditions causing negative dysphotopsia have been proposed but they do not address light passing through a gap between the iris and intraocular implant lens. For instance, U.S. Patent Application Publication No. 2008/0269891 A1 describes an intraocular lens with modified edge characteristics that inhibit transverse propagation of internally reflected light rays. However, while this publication treats one possible cause of negative dysphotopsia, it does not address light passing through a gap between the iris and intraocular implant lens. With respect to addressing the gap, some have proposed implanting an intraocular implant lens in the ciliary sulcus rather than in the capsular bag. Others have proposed implanting an additional low or no powered clear intraocular implant lens in the ciliary sulcus while a prior implanted intraocular implant lens remains in the capsular bag.

SUMMARY

The present disclosure relates to an ophthalmic prosthetic, which may address at least some of the needs identified above, the ophthalmic prosthetic may comprise a peripheral light-blocking implant member adapted to locate in a gap between and its contiguous ciliary body and an iris and an intraocular implant lens. The gap may be located between the anterior surface of the intraocular implant lens and the posterior surface of the iris or an internal surface of the contiguous ciliary body. The peripheral light-blocking implant member may be selectively positioned to block passage of light. The gap may be an axial gap, a radial gap, or both The peripheral light-blocking implant member may be opaque, partially opaque, translucent, polarized, or any combination thereof. The peripheral light-blocking implant member may be frosted.

A thickness of the peripheral light-blocking implant member may be from about 0.01 mm to about 1.2 mm (e.g., from about 0.1 mm to about 1 mm; or from about 0.2 mm to about 0.8 mm).

The peripheral light-blocking implant member may be an annular sector. The annular sector may be configured to locate in the nasal hemisphere of an eye, a temporal hemisphere of an eye, or both. The peripheral light-blocking implant member may be annular.

The peripheral light-blocking implant member may be integral to the ophthalmic prosthetic. The peripheral light-blocking implant member may be artificially fabricated.

The peripheral light-blocking implant member may include an aperture. The aperture may be an optically clear material portion of the peripheral light-blocking implant member or a through-hole extending through the peripheral light-blocking implant member.

A diameter of the aperture may be from about 1.5 mm to 6 mm (e.g., from about 2 mm to about 5 mm, from about 3 mm to about 4 mm).

The peripheral light-blocking implant member may include one or more surface modifications located on or adjacent to the inner perimeter.

The ophthalmic prosthetic may be flexible, foldable, compressible, dehydratable, rehydratable or any combination thereof.

The ophthalmic prosthetic may be partially opaque.

The ophthalmic prosthetic may be functionally polarizing or partially polarizing.

The ophthalmic prosthetic may further comprise one or more haptics. The haptics may be configured to prevent the ophthalmic prosthetic from moving or rotating within an eye. The one or more haptics may be elongate projections that extend radially from the outer perimeter of the ophthalmic prosthetic. The shape of the one or more haptics may be generally C-shaped, J-shaped, plate-shaped, or any combination thereof.

The present disclosure relates to a method for correcting negative and/or positive dysphotopsia for a person in need of correction of or at risk for negative and/or positive dysphotopsia caused by light passing between an iris and intraocular lens. The method may address at least some of the needs identified above. The method may comprise forming an incision in a cornea, inserting an ophthalmic prosthetic into an eye through the incision, and locating the ophthalmic prosthetic between the iris and the intraocular lens.

The ophthalmic prosthetic or at least a sector thereof may be located in the nasal hemisphere of an eye, a temporal hemisphere of an eye, or both. The method may further comprise fixating the ophthalmic prosthetic to one or more structures of the eye. The ophthalmic prosthetic may be passively fixated within a capsular bag or a ciliary sulcus. The ophthalmic prosthetic may be fixated via a periphery of the ophthalmic prosthetic, haptics, sutures, or any combination thereof.

The method may further include rolling the ophthalmic prosthetic into a roll having a major diameter no greater than 3 mm.

DETAILED DESCRIPTION

Figure 1:
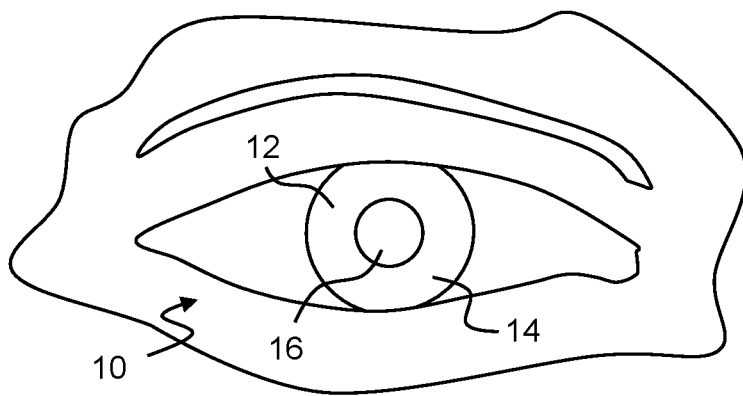
FIG. 1 is a plan view of an eye.

The present teachings may meet one or more of the above needs by the improved ophthalmic prosthetic and method for correcting negative and/or positive dysphotopsia described herein. The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present disclosure provides for an ophthalmic prosthetic and a method for correcting or providing prophylaxis against negative and/or positive dysphotopsia. The ophthalmic prosthetic may be surgically implanted in the eye of a person in need of correction of negative and/or positive dysphotopsia. The ophthalmic prosthetic may be surgically implanted in the eye of a person who is planning to undergo cataract surgery and may have one or more risk factors for the development of negative and/or positive dysphotopsia. The risk factors for negative and/or positive dysphotopsia may be based on characteristics of an individual eye, dysphotopsia in a fellow eye of the same individual, or both. The ophthalmic prosthetic may be surgically implanted in the eye of a person in need of correction of negative and/or positive dysphotopsia caused by light passing between a gap between an iris and an intraocular implant lens. The intraocular implant lens may be artificially fabricated. The intraocular lens may be surgically implanted in an individual. The ophthalmic prosthetic may be surgically implanted in the eye of a person in need of correction of negative and/or positive dysphotopsia caused by light passing between a gap between an iris and an intraocular implant lens resulting from a procedure of removal during cataract surgery, genetic disorders causing birth without a natural lens, or dislocation of an intraocular implant lens by an injury and/or genetic susceptibility to dislocation of an intraocular implant lens. The gap may arise from the position in which an intraocular implant lens is surgically implanted in the eye. The gap may arise from positional shifting of an intraocular lens within the eye during or after the surgical procedure. Patient in need, as referred to herein, may be defined as a person having one or more of the above-mentioned defects.

The gap may be an axial gap, a radial gap, or both. The axial gap may be defined by a length between an iris and an intraocular implant lens along an axis that is parallel to the visual axis. The radial gap may be defined by a length between the visual axis and a peripheral interior wall of an eye.

Light entering the eye along a path that is oblique (e.g., tangential) to the intraocular implant lens (e.g., between about 1° and 89° from the optical axis of the eye) can pass through a gap between an iris and an intraocular implant lens unimpeded and the light may strike an anterior portion of the nasal retina. Light entering the eye along a path that is oblique (e.g., tangential) to the intraocular implant lens (e.g., between about 1° and 89° from the optical axis of the eye) can strike the edge of the intraocular implant lens and be deflected, reflected, and/or refracted toward an anterior portion of the nasal retina. Light entering the eye can strike the edge of the intraocular implant lens and be refracted posteriorly within the eye toward the posterior retina. The space between the posteriorly refracted rays and the rays which pass through the gap unimpeded, may result in a gap in illumination of the anterior portion of the nasal retina, which patients may perceive as a temporal dark area in their vision. Some patients report of the area being crescent-shape although other shapes may be possible. This condition is conventionally referred to as negative dysphotopsia. Light that strikes the edge of the intraocular implant lens and is deflected, reflected, and/or refracted toward an anterior portion of the nasal retina may result in positive light related symptoms. These positive light related symptoms can be perceived as arcs, glare, halos, starbursts or other positive bright light phenomena collectively referred to as positive dysphotopsias. Positive dysphotopsias may occur in any meridian of the eye and may affect peripheral or more central aspects of the visual field.

The ophthalmic prosthetic of the present disclosure may comprise a peripheral light-blocking implant member configured to locate in a gap between the anterior intraocular implant lens periphery and the posterior iris periphery. More specifically, the peripheral light-blocking implant member may be configured to locate in a gap between the anterior intraocular implant lens periphery and ciliary sulcus periphery or capsular bag periphery. The peripheral light-blocking implant member may fill all or part of this gap. The peripheral light-blocking implant member or at least a portion thereof may be selectively positioned in the eye to block the passage of light.

The ophthalmic prosthetic of the present disclosure may function to at least partially block the passage of light rays through a gap between an iris and an intraocular implant lens, at least partially block the passage of light rays striking the edge or other portion of the intraocular implant lens, or both. The ophthalmic prosthetic may create a barrier to oblique light striking or bypassing the anterior edge of an intraocular implant lens. The barrier may mask the intraocular implant lens edge and/or aphakic space peripheral to the intraocular implant lens edge or fill the gap between the posterior portion of the iris and the anterior portion of the intraocular implant lens, thereby preventing light from entering the peripheral space.

The peripheral light-blocking implant may block light travelling oblique to the iris plane, while light passing along or near the optical axis may pass through the device unimpeded. This could be achieved by polarization or micro-fenestrations in the peripheral light-blocking component of the implant.

The ophthalmic prosthetic may be fabricated from a biocompatible material. The ophthalmic prosthetic may be fabricated from a polymer. The biocompatible polymer may include polymethylmethacrylate, polycarbonate, polyvinylidene fluoride, polyvinyl chloride, polypropylene, polyethylene, polystyrene, polyether ether ketone, polysulfone, polyimide, prolene, hydrophilic acrylic, hydrophobic acrylic, hydrogel, silicone, the like, or any combination thereof. The ophthalmic prosthetic may be fabricated from carbon fiber.

The ophthalmic prosthetic may be defined by a thickness. The thickness may be measured between an anterior surface and posterior surface of the ophthalmic prosthetic. The anterior surface may oppose the posterior surface. The anterior surface may be oriented toward the anterior portion of the eye after implantation into a living being. The posterior surface may be oriented toward the posterior portion of the eye after implantation into a living being. The thickness may be between about 0.01 mm and 1.2 mm. The thickness may be about 0.01 mm or more, 0.1 mm or more, or even 0.2 mm or more. The thickness may be about 1.2 mm or less, 1 mm or less, 0.8 mm or less, or even 0.6 mm or less. The ophthalmic prosthetic may have a uniform thickness. The ophthalmic prosthetic may have a thickness that varies from an inner perimeter to an outer perimeter. The ophthalmic prosthetic may vary in thickness radially, concentrically, or may vary in thickness in a non-uniform fashion. The variation of thickness may be gradual. The variation of thickness may be continuous and/or step-wise. The thickness may have tolerances in conformance with ISO 11979-3.

The ophthalmic prosthetic may maintain its dimensional properties (e.g., diameter and/or thickness) and structural integrity (e.g., free of tearing) after implantation into a patient's eye. The ophthalmic prosthetic may maintain its dimensional properties (e.g., diameter and/or thickness) and structural integrity (e.g., free of tearing) after surgical manipulation (e.g., surgical implantation) with an intraocular lens injector and/or cartridge according to the present teachings. The ophthalmic prosthetic may maintain its dimensional properties (e.g., diameter and/or thickness) and structural integrity (e.g., free of tearing) after surgical manipulation with forceps (e.g., surgical implantation or removal) in conformance with ISO 11979-3.

The ophthalmic prosthetic may include a curvature. The curvature may correspond to a curvature of a focusing element (e.g., intraocular lens). The curvature may be customized to generally correspond to the curvature of an individual patient's intraocular lens. The curvature may contribute, at least in part, to the focusing of light rays that enter the eye. The anterior surface may be convex. The posterior surface may be concave, convex, or flat.

The ophthalmic prosthetic may have a generally uniform surface roughness on the anterior surface, posterior surface, or both. The ophthalmic prosthetic may have a generally uniform surface roughness on the inner perimeter, outer perimeter, or both. As referred to herein, a generally uniform surface roughness may mean an average roughness ($S_a$) of about 10 nm or less. That is, an average of absolute values of the surface differences in a given area may be about 10 nm or less from a mean plane. Surface roughness (topography) may be measured according to the method set forth in Lewandowska et. al., The technique of measurement of intraocular lens surface roughness using Atomic Force Microscopy, Interdisciplinary Journal of Engineering Sciences, Vol. II, No. 1 (2014), incorporated herein by reference for all purposes.

The ophthalmic prosthetic may comprise a fiber portion, as described herein. An ophthalmic prosthetic that is free of a fiber portion may have a tear strength of about 30 mN or more, 50 mN or more, or even 70 mN or more. An ophthalmic prosthetic that is free of a fiber portion may have a tear strength of about 130 mN or less, 110 mN or less, or even 90 mN or less. An ophthalmic prosthetic that includes a fiber portion may have a tear strength of about 300 mN or more, 500 mN or more, or even 700 mN or more. An ophthalmic prosthetic that includes a fiber portion may have a tear strength of about 1,300 mN or less, 1,100 mN or less, or even 900 mN or less.

The ophthalmic prosthetic may be custom-fabricated for different patients. The custom fabrication may include a custom dimensions (e.g., diameter and/or thickness), custom color of the peripheral light-blocking implant member, custom number and configuration of haptics, custom profile shape (e.g., circular, elliptical, and/or ovoid), or any combination thereof. For example, the dimensions may be customized to suitably fit the dimensions of a patient's eye. The ophthalmic prosthetic may substantially mimic the color and appearance of a patient's eye without the ophthalmic prosthetic.

The ophthalmic prosthetic may be foldable, flexible, rollable, compressible, dehydratable, or any combination thereof. The ophthalmic prosthetic may be sufficiently foldable, flexible, rollable, compressible, and/or dehydratable to be insertable into an eye through an incision no greater than 8 mm in the largest dimension, more preferably 6 mm, or even more preferably 3 mm. As referred to herein with reference to an incision, the largest dimension may be the length between two opposing ends of the incision. The ophthalmic prosthetic may be rollable into a roll having an outermost diameter of no greater than 3 mm. The ophthalmic prosthetic may be foldable into a bi-fold, tri-fold, or even quad-fold of no greater than 3 mm in the largest dimension. The ophthalmic prosthetic may be elastic. That is, after folding, flexing, rolling, compressing, and/or dehydrating the ophthalmic prosthetic, it may return to its pre-deformed dimensions. The ophthalmic prosthetic may be rehydratable.

The ophthalmic prosthetic may be insertable into an eye by any suitable intraocular lens injector. As a non-limiting example, the intraocular lens injector may include a handpiece. The handpiece may include a plunger rod (which may be spring-loaded) with an actuator (e.g., a screw-style actuator adapted for a push and twist motion) for delivering the device (e.g., via a cartridge). One commercial example of such a device is the UNFOLDER® Silver, commercially available from Johnson & Johnson. The intraocular lens injector may be employed with a cartridge. As a non-limiting example, the cartridge may include the PSCST cartridge, commercially available from Johnson & Johnson. After introduction into the eye, the ophthalmic prosthetic may un-folded, un-flexed, un-compressed, and/or un-rolled. Elastic properties of the ophthalmic prosthetic may cause it to at least partially un-fold, un-flex, un-compress, and/or un-roll without manipulation by an optometric physician. The ophthalmic prosthetic may be manipulated by an optometric physician to un-fold, un-flex, un-compress, and/or un-roll the ophthalmic prosthetic.

The ophthalmic prosthetic may be placed in the ciliary sulcus, between the posterior iris and anterior aspect of the capsular bag. The ophthalmic prosthetic may be placed within the capsular bag between the posterior side of the anterior capsule and anterior surface of the intraocular lens. The ophthalmic prosthetic may be placed within the capsular bag between the anterior side of the posterior capsule and posterior surface of the intraocular lens (behind the intraocular lens).

The ophthalmic prosthetic may comprise one or more peripheral light-blocking implant members, one or more interior light transmitting portions, an inner perimeter, one or more surface modifications, an outer perimeter, an anterior portion, a posterior portion, one or more fiber portions, one or more haptics, or any combination thereof.

The ophthalmic prosthetic may comprise one or more peripheral light-blocking implant members. The peripheral light-blocking implant member may function to at least partially block the passage of light rays through a gap between an iris and intraocular lens relative to an eye free of an ophthalmic prosthetic according to the present teachings.

The peripheral light-blocking implant may limit the light access to the peripheral aphakic space by extending far enough into the periphery of the ciliary sulcus and/or the periphery of the capsular bag so that the light rays cannot reach the anterior portion of the nasal retina.

The peripheral light-blocking implant member may be optically opaque or at least partially optically opaque to visible light (i.e., light having a wavelength of from about 390 nm to 700 nm). As referred to herein, the term "opaque" may mean preventing or at least substantially reducing the transmission of radiant energy (e.g., light), by absorption and/or reflection of the radiant energy. As referred to herein, a material and/or structure that is opaque may have a light transmissivity of about 30% or less, more preferably 20% or less, more preferably 10% or less, or even more preferably 5% or less. The peripheral light-blocking implant member may be transparent to light in an infrared range (i.e., light having a wavelength of from about 750 nm to 1,000 µm). As referred to herein, a material and/or structure that is transparent may have a light transmissivity of about 70% or more, more preferably 80% or more, more preferably 90% or more, or even more preferably 100%.

The peripheral light-blocking implant member may have a uniform transmissivity across one or more dimensions (e.g., diameter and/or thickness). The peripheral light-blocking implant member may have two or more regions of varying transmissivity. Transmissivity may vary gradually or step-wise. For example, the transmissivity may gradually increase from the inner perimeter of the peripheral light-blocking implant member to the outer perimeter of the peripheral light-blocking implant member, or vice versa. The transmissivity may vary over one or more ranges in different regions of the peripheral light-blocking implant member. That is, one region may vary in transmissivity by 30%, from one end of the region to an opposing end of the region, while another region may vary in transmissivity by 10%, from one end of the region to an opposing end of the region. The transmissivity may vary over smaller ranges in regions proximate to the inner perimeter, outer perimeter, or both.

The peripheral light-blocking implant member may be fabricated from a material (e.g., polymer) treated with dye, pigment, or both. Dyes may refer to substances soluble in solvent that are typically optically transparent and absorb but do not scatter light. Pigments may refer to powdered substance suspensions. Pigments may generally be more optically opaque than dyes. The dye, pigment, or both may be a biologically inert substance. The dye, pigment, or both may be approved by the FDA. Exemplary, non-limiting dyes and pigments may include those enumerated in 21 C.F.R. Part 73, Subpart D and 21 C.F.R. Part 74, Subpart D, incorporated herein by reference in their entirety for all purposes. The concentration of dye and/or pigment may modulate the transmissivity and/or absorption of the annular portion. The chemical identity of the dye and/or pigment may modulate the wavelengths of light absorbed by the dye and/or pigment.

The peripheral light-blocking implant member may be fabricated from a material (e.g., polymer) with optically opaque particulates dispersed therein. The optically opaque particulates may include carbon nanoparticles. The optically opaque particles may be dispersed in a polymer in a liquid state. The dispersion of optically opaque particles may be positionally fixed by hardening and/or cross-linking of the polymer. The optically opaque particulates may be in the form of spheres, rods, whiskers, horns, pyramids, the like, or any combination thereof. The optically opaque particulates may be about 10 nm or more, 20 nm or more, 30 nm or more, or even 40 nm or more in their largest dimension. The optically opaque particulates may be about 100 nm or less, 90 nm or less, 80 nm or less, 70 nm or less, or even 60 nm or less in their largest dimension.

The peripheral light-blocking implant member may be fabricated from a naturally optically opaque material. The naturally opaque material may include films. The films may include carbon films, metal films, polymer films, or any combination thereof. The film may be located on an anterior portion and/or posterior portion of the peripheral light-blocking implant member. The film may be encapsulated in a polymer of the peripheral light-blocking implant member. The film may have a thickness of about 1 μm or more, 5 μm or more, 10 μm or more, or even 20 μm or more. The film may have a thickness of about 500 μm or less, 300 μm or less, 100 μm or less, or even 50 μm or less.

One or any combination of dye and/or pigment, optically opaque particulates, and naturally optically opaque materials, as taught herein, may be employed in an ophthalmic prosthetic. For example, an ophthalmic prosthetic may comprise a peripheral light-blocking implant member fabricated from both of a dye and/or pigment and optically opaque particles.

An anterior surface, posterior surface, outer perimeter, and/or inner perimeter of the peripheral light-blocking implant member may be subjected to material removal, material addition, or both, according to the present teachings. Material removal and/or material addition may influence transmissivity, absorption, or reflection of the annular portion, or any combination thereof. For example, chemical etching may reduce the transmissivity of the peripheral light-blocking implant member.

Transmissivity of the peripheral light-blocking implant member may be modulated by increasing or decreasing the concentration of dyes and/or pigments, optically opaque particles, or any combination thereof.

The thickness of the peripheral light-blocking implant member may be between about 0.01 mm and 1.2 mm. The thickness of the peripheral light-blocking implant member may be about 0.01 mm or more, 0.1 mm or more, or even 0.2 mm or more. The thickness of the peripheral light-blocking implant member may be about 1.2 mm or less, 1 mm or less, 0.8 mm or less, or even 0.6 mm or less. Transmissivity of the peripheral light-blocking implant member may be modulated by increasing or decreasing the thickness of the peripheral light-blocking implant member.

The peripheral light-blocking implant member may be defined by a diameter of a circle or length of a major axis of an oval or ellipse. The diameter or length of the major axis may be greater than a diameter of a patient's pupil. The diameter or length of the major axis may be greater than, generally equal to, or less than a diameter of a capsular bag of a patient's eye. The diameter may be greater than, generally equal to, or less than a diameter of a ciliary sulcus of a patient's eye. The diameter may be between about 1 mm and 6 mm. The diameter may be about 1 mm or more, 1.5 mm or more, 2 mm or more, or even 2.5 mm or more. The diameter may be about 6 mm or less, 5.5 mm or less, 5 mm or less, or even 4.5 mm or less.

The peripheral light-blocking implant member may have an annular profile. The annular profile may or may not be contiguous for 360°. The peripheral light-blocking implant member may be sectoral. That is, the peripheral light-blocking implant member may be an annular sector contiguous for an angle of less than 360°. The peripheral light-blocking implant member may be radially symmetric. The peripheral light-blocking implant member may be radially asymmetric.

Figure 7:
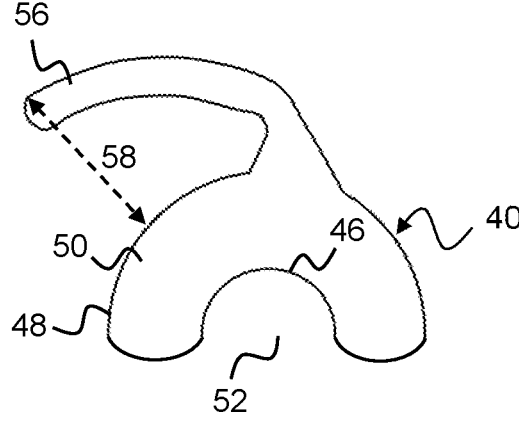
FIG. 7 is a plan view of an ophthalmic prosthetic according to the present disclosure.

The peripheral light-blocking implant member may have a profile that is an annular sector. The annular sector may be defined by an angle. The angle may be about 1° or more 5° or more 100 or more, 300 or more, 600 or more, or even 900 or more. The angle may be about 3500 or less, 3000 or less, 2500 or less, 2000 or less, 1500 or less, or even 1000 or less. For example, the annular sector may have an angle of about 180°, as illustrated in FIG. 7.

The ophthalmic prosthetic may comprise one or more interior light transmitting portions. The interior light trans-mitting portion may function to allow passage of light to the retina and/or fovea. The interior light transmitting portion may be located within the peripheral light-blocking implant member. The interior light transmitting portion may be generally concentric with the peripheral light-blocking implant member (i.e., co-linear central axes). A central axis of the interior light transmitting portion may be offset from a central axis of the peripheral light-blocking implant member. The interior light transmitting portion may include an aperture or a portion of optically transparent material. As referred to herein, a material and/or structure that is transparent may have a light transmissivity of about 70% or more, more preferably 80% or more, more preferably 90% or more, or even more preferably 100%. The aperture may be free of material (e.g., through-hole).

The interior light transmitting portion may be defined by a central axis extending transversely through its geometric center. The central axis of the interior light transmitting portion may be coaxial with an optical axis of the eye. The central axis of the interior light transmitting portion may be offset from an optical axis of the eye. The central axis may be offset by about 0.001 mm or more, 0.005 mm or more, or even 0.01 mm or more from an optical axis of the eye. The central axis may be offset by about 1 mm or less, 0.5 mm or less, or even 0.1 mm or less from an optical axis of the eye.

The central axis of the interior light transmitting portion may be coaxial with the central axis of the pupil. The central axis of the interior light transmitting portion may be offset from the central axis of the pupil. The central axis may be offset by about 0.001 mm or more, 0.005 mm or more, or even 0.01 mm or more from the central axis of the pupil. The central axis may be offset by about 1 mm or less, 0.5 mm or less, or even 0.1 mm or less from the central axis of the pupil.

The interior light transmitting portion may be defined by a diameter of a circle or a length of a major axis of an oval or ellipse. The diameter or length of a major axis may be generally equal to the diameter of the inner perimeter. The diameter or length of a major axis may be between about 0.05 mm and 3 mm. The diameter or length of a major axis may be about 0.05 mm or more, 0.1 mm or more, 0.5 mm or more, or even 1 mm or more. The diameter or length of a major axis may be about 3 mm or less, 2.5 mm or less, 2 mm or less, or even 1.5 mm or less. The diameter or length of a major axis may be generally equal to, less than, or greater than a diameter of a pupil.

The ophthalmic prosthetic may include an inner perimeter. The inner perimeter may extend between an anterior surface and posterior surface of the ophthalmic prosthetic. The inner perimeter may be radially distanced from the outer perimeter of the ophthalmic prosthetic. The inner perimeter may circumscribe the interior light transmitting portion.

The inner perimeter may be generally perpendicular to the anterior surface, posterior surface, or both. The inner perimeter may slope from the anterior surface to the posterior surface, or vice versa. The slope may extend at an angle from an orthogonal axis of the anterior surface and/or posterior surface. The angle may be about 1° or more, 2° or more, 5° or more, or even 10° or more. The angle may be about 45° or less, 40° or less, 300 or less, or even 20° or less. The inner perimeter may have a curvature. The inner perimeter may be convex or concave with respect to the interior light transmitting portion.

The inner perimeter may be defined by a length, as measured between the anterior surface and posterior surface of the ophthalmic prosthetic. The length may be between about 0.1 mm and 1 mm. The length may be about 0.1 mm or more, 0.2 mm or more, or even 0.3 mm or more. The length may be about 1 mm or less, 0.8 mm or less, 0.7 mm or less, or even 0.6 mm or less.

The ophthalmic prosthetic may comprise surface modifications. The surface modifications may function to reduce or substantially eliminate uniform diffraction of light as compared to an ophthalmic prosthetic without the surface modifications of the present disclosure. The surface modifications may reduce the chances of diffraction-related phenomena. The surface modifications may absorb light, reflect light internally, reflect light away from the eye, cause the spread of diffracted light across the retina, cause non-uniform diffraction, or any combination thereof. Internal reflection of light may refer to a repetitive reflection between two or more adjacent and opposingly oriented surfaces that propagates in a direction that is generally radially outward (i.e., toward the outer perimeter of the ophthalmic pinhole prosthetic). Each iteration of repetitive reflection may result in the absorption of at least a portion of the light ray by the ophthalmic pinhole prosthetic.

The surface modifications may be located on the peripheral light-blocking implant member. The surface modifications may be located on or proximate to the inner perimeter. The surface modifications may be disposed on the interior light transmitting portion proximate to the inner perimeter, the annular portion proximate to the inner perimeter, or both.

The surface modifications may be between about 0.1 μm to 1,000 μm in their largest dimension. The surface modifications may be about 0.1 μm or more, 1 μm or more, 10 μm or more, 50 μm or more, or even 100 μm or more in their largest dimension. The surface modifications may be about 1,000 μm or less, 750 μm or less, 500 μm or less, or even 250 μm or less in their largest dimension.

The largest dimension, referring to the colors, may be the length between the two most distanced points of the surface area occupied by a portion of color. For example, the largest dimension of colors disposed as dots on the surface of the ophthalmic prosthetic may be the diameter of the dot.

The largest dimension, referring to the shapes, may be the length between the two most distance points of the surface area occupied by a shape, the distance a groove extends into a surface of the ophthalmic pinhole prosthetic, the distance a ridge extends from a surface of the ophthalmic prosthetic, the distance between adjacent crests, the distance between adjacent troughs, or any combination thereof.

The largest dimension, referring to the surface topography, may be the distance a groove extends into a surface of the ophthalmic pinhole prosthetic, the distance a ridge extends from a surface of the ophthalmic pinhole prosthetic, the distance between adjacent crests, the distance between adjacent troughs, or any combination thereof.

The largest dimension, referring to the opacity gradient, may be the length of the annular region occupied by the opacity gradient from its inner diameter to its outer diameter.

The surface modifications may comprise one or more colors, one or more patterns of shapes, one or more surface topographies, one or more opacity gradients, or any combination thereof.

The surface modifications may comprise one or more colors. The colors may be characterized by a wavelength. The colors may include any color in the CMYK color space. The colors may be characterized by hue, chroma, intensity, saturation, luminance, brightness value, opacity, or any combination thereof. The colors may include two or more colors, three or more colors, four or more colors, or even five or more colors.

The color may be imparted by dye, pigment, or both. Dyes may refer to substances soluble in solvent that are typically optically transparent and absorb but do not scatter light. Pigments may refer to powdered substance suspensions. Pigments may generally be more optically opaque than dyes. The dye, pigment, or both may be a biologically inert substance. The dye, pigment, or both may be approved by the FDA. Exemplary, non-limiting dyes and pigments may include those enumerated in 21 C.F.R. Part 73, Subpart D and 21 C.F.R. Part 74, Subpart D, incorporated herein by reference for all purposes.

It may be particularly advantageous to prevent dyes and/or pigments from bleeding or leaching into the ophthalmic pinhole prosthetic or the eye. The dye and/or pigment may have a suitably high covalency to prevent bleeding or leaching. The dye and/or pigment may be surface bonded to the ophthalmic pinhole prosthetic. The dye and/or pigment may be surface bonded to the peripheral light-blocking implant member. Surface bonding may involve providing a dye and/or pigment with a linking chemical moiety and grafting the same to the polymer of the ophthalmic prosthetic after polymerization. The dye and/or pigment may be diffused into the polymer matrix of the ophthalmic prosthetic. The dye and/or pigment may be diffused into the polymer matrix of the peripheral light-blocking implant member. Dye and/or pigment may be applied to an ophthalmic prosthetic and a coating (e.g., thin film) may be located over the dye and/or pigment to prevent or at least substantially prevent bleeding or leaching.

The colors may be disposed on surfaces of the ophthalmic prosthetic in the form of one or more shapes. Typically, the colors may be in the form of dots however other shapes are contemplated by the present disclosure. The colors may be continuous across one or more surfaces of the ophthalmic pinhole prosthetic. The shapes (e.g., dots) may be produced by inkjet printing. The shape of the colors may be determined by a template, as taught herein. Inkjet printing may produce dots of dye and/or pigment having a diameter of between about 50 μm and 500 μm. The diameter may be about 50 μm or more, 100 μm or more, 150 μm or more, or even 200 μm or more. The diameter may be about 500 μm or less, 450 μm or less, 400 μm or less, 350 μm or less, or even 300 μm or less.

Two or more colors may be spaced from one another, overlap with one another, or both. Overlapping of or adjacent two or more colors may produce a color that is different from the two or more colors. For example, overlapping or adjacent red and blue may produce purple.

The colors may be selected to absorb light of one or more different wavelengths. Selectively employing colors to absorb light of particular wavelengths may modulate the diffraction pattern generated by the inner perimeter.

The surface modifications may comprise one or more patterns of shapes. The patterns of shapes may be a generally uniform pattern (i.e., uniform shape(s), orientation of shapes, and/or spacing between shapes). The shapes may include any suitable geometric shape. The shapes may include any 3-sided, 4-sided, 5-sided, 6-sided, 7-sided, or even 8-sided shape (e.g., polygon). The shapes may include an amorphous shape. It may be particularly advantageous for the shapes to include amorphous shapes. The amorphous shape may have a geometry with one or more undulations, lobes, sides, corners, or any combination thereof.

The one or more patterns of shapes may be defined by grooves extending into the ophthalmic pinhole prosthetic from the inner perimeter, ridges extending from the inner perimeter, a surface area occupied by dye/pigment, or any combination thereof. The grooves, ridges, dye/pigment, or any combination thereof may be disposed around the profile of the shapes where the internal area of the shapes may be free of the same. The grooves, ridges, dye/pigment, or any combination thereof may be disposed throughout the area of the shapes.

The patterns of shapes may be apparent to a viewer from a viewing angle that is at least orthogonal to the surface of the inner perimeter.

The grooves and/or ridges may function to alter the light (e.g., light which would create a detectable image that is perceived by a patient) as compared to an inner perimeter without the grooves and/or ridges. For example, the grooves and/or ridges may function to scatter, absorb, and/or reflect light differently as compared to an inner perimeter without the grooves and/or ridges.

The one or more patterns of shapes may be fabricated on or in the inner perimeter by material removal and/or material addition, as taught herein.

The surface modifications may comprise one or more surface topographies. The surface topography may be defined by a plurality of crests and troughs formed in surfaces of the ophthalmic prosthetic and facets extending between crests and troughs. The surface topography may be defined by a plurality of crests and troughs formed in surfaces of the peripheral light-blocking implant member and facets extending between crests and troughs. The crests and/or troughs may be curved, pointed, or both. The crests and/or troughs may extend a length from a mean plane. The mean plane may be defined by an average plane between crests and troughs. Different portions of the inner perimeter may include surface topographies, or the inner perimeter may have a uniform surface topographies over the entire inner perimeter.

The crests and troughs may project from the anterior surface to the posterior surface of the ophthalmic pinhole prosthetic. That is, individual crests and troughs may extend the length between the anterior surface to the posterior surface of the ophthalmic prosthetic. Individual crests and troughs may extend the length between the anterior surface to the posterior surface of the peripheral light-blocking implant member. When viewed along a viewing angle orthogonal to the anterior surface or posterior surface of the ophthalmic prosthetic, the crests and troughs may both be visible to the viewer.

The crests and troughs may project perimetrically around the inner perimeter. That is, individual crests and troughs may extend the length around the inner perimeter. When viewed along a viewing angle orthogonal to the anterior surface or posterior surface of the ophthalmic prosthetic, the foremost crest and facet may be visible to the viewer.

The crests and troughs may be randomly distributed across the surface of the inner perimeter. That is, a plurality of crests and troughs may be disposed along the length between the anterior and posterior surfaces of the ophthalmic pinhole prosthetic and/or perimetrically around the inner perimeter. The randomly distributed crests and troughs may not be disposed in any discernable rows, layers, or otherwise.

The surface topography may be scalloped. Scalloped may mean crests that are curved, and troughs are pointed, with the troughs being disposed at the interface of curvature radii of adjacent crests; or troughs that are curved and crests that are pointed, the crests being disposed at the interface of curvature radii of adjacent troughs.

The surface topography may be jagged. Jagged may mean crests and troughs that are both pointed. Facets between points may be straight, curved, or both.

The surface topography may be irregular. Irregular may mean a random distribution of pointed crests, curved crests, pointed troughs, curved troughs, straight facets, curved facets, or any combination thereof.

The surface topography may be generally uniform. That is, the crests and troughs may extend a generally uniform length above and/or below a mean plane, have generally the same shape (e.g., pointed and/or curved), have generally equal distances between adjacent crests and/or troughs, or any combination thereof.

The surface topography may vary. That is, the crests and troughs may extend different lengths above and/or below a mean plane, have different shapes (e.g., pointed and/or curved), have different distances between adjacent crests and/or troughs, or any combination thereof.

The surface topography may function to alter the light (e.g., light which would create a detectable image that is perceived by a patient) as compared to an inner perimeter without the surface topography. For example, the surface topography may function to scatter, absorb, and/or reflect light differently as compared to an inner perimeter without the surface topography.

The one or more surface topographies may be fabricated on or in the inner perimeter by material removal and/or material addition, as taught herein.

The one or more surface modifications may include one or more opacity gradients. The opacity gradient may decrease in opacity from the annular portion to the interior light transmitting portion. The opacity gradient may decrease in opacity from the posterior surface of the ophthalmic pinhole prosthetic to the posterior surface of the ophthalmic pinhole prosthetic or vice versa. The opacity may decrease by about 10% or more, 30% or more, or even 50% or more. The opacity may decrease by about 100% or less, 90% or less, or even 70% or less.

The opacity gradient may be located in both a region of the annular portion and a region of the interior light transmitting portion. By way of example, the opacity gradient may extend into an interior light transmitting portion that is fabricated from optically transparent material. The opacity gradient may be located in an annular gradient region located in both the annular portion and the interior light transmitting portion. The annular gradient region may be defined by a length from its inner diameter to its outer diameter. The length may be about 0.01 mm or more, 0.05 mm or more, or even 0.1 mm or more. The length may be about 1 mm or less, 0.5 mm or less, or even 0.3 mm or less.

The opacity gradient may be fabricated by varying a concentration of dye and/or pigment, a concentration of optically opaque particulates, a thickness of a film, a depth of etching, or any combination thereof. The dye and/or pigment, optically opaque particulates, film, and etching may be identified and/or applied to the ophthalmic prosthetic according to the teachings herein. The dye and/or pigment, optically opaque particulates, film, and etching may be identified and/or applied to the peripheral light-blocking member according to the teachings herein.

The ophthalmic prosthetic may comprise an outer perimeter. The outer perimeter may extend between an anterior surface and posterior surface of the ophthalmic prosthetic. The outer perimeter may be radially distanced from the inner perimeter.

The outer perimeter may be generally perpendicular to the anterior surface, posterior surface, or both. The outer perimeter may slope from the anterior surface to the posterior surface, or vice versa. The slope may extend at an angle from an orthogonal axis of the anterior surface and/or posterior surface. The angle may be about 1° or more, 2° or more, 5° or more, or even 10° or more. The angle may be about 450 or less, 40° or less, 30° or less, or even 200 or less. The outer perimeter may have a curvature. The outer perimeter may be convex or concave with respect to the interior light transmitting portion. The outer perimeter may be flat.

The outer perimeter may be defined by a diameter of a circle or length of a major axis of an oval or ellipse. The diameter or length of a major axis may be between 9 mm and 15 mm. The diameter or length of a major axis may be about 9 mm or more, 10 mm or more, 10.5 mm or more, 11 mm or more, or even 11.5 mm or more. The diameter or length of a major axis may be about 15 mm or less, 14 mm or less, 13.5 mm or less, 13 mm or less, or even 12.5 mm or less.

The ophthalmic prosthetic may include one or more haptics. The haptics may function to prevent the ophthalmic prosthetic from moving or rotating within the eye. The haptics may extend radially from the outer perimeter of the ophthalmic prosthetic. The haptics may be generally elongate projections that extend radially from the outer perimeter of the ophthalmic prosthetic. The arms may extend orthogonal or at any acute angle to a tangent of the outer perimeter. Arms may curve toward and or away from the outer perimeter. The haptics may be C-shaped, J-shaped, plate-shaped, or any other suitable design.

The haptics, when implanted into a living being, may be opposed against an inner surface of an eye. For example, the haptics may oppose against a perimeter of a capsular bag, posterior chamber, or anterior chamber. The haptics may be elastic. The diameter of elastic haptics may be larger than a diameter of an eye structure (e.g., perimeter of the anterior chamber) so that the haptics deform when located within the eye and apply pressure against the eye structure. The diameter of elastic haptics may be 0.1%, 0.5%, 1%, 2%, 3%, 5%, or even 10% larger than the diameter of an eye structure.

The haptics, when implanted into a living being, may be mounted to an eye structure via sutures. The haptics may be employed with sutures to prevent the prosthetic from moving or rotating within the eye. The haptics may include elongated projections that extend radially from the outer perimeter of the ophthalmic prosthetic.

The haptics may extend from the outer perimeter of the ophthalmic prosthetic. The haptics may extend a length radially from the outer perimeter of the ophthalmic prosthetic. The length may be between about 3 mm and 10 mm). The length may be about 3 mm or more, 4 mm or more, or even 6 mm or more. The length may be about 10 mm or less, 9 mm or less, or even 8 mm or less.

The ophthalmic prosthetic described herein may include one, two, three, four, or more haptics. The haptics may be located equidistant with respect to each other around the outer perimeter. The haptics may be located at different distances from each other around the outer perimeter. The haptics may be located on opposing sides of the outer perimeter.

The haptics may be co-planar with the outer perimeter. The haptics may be oriented at an angle to the plane of the outer perimeter. The angle may be about 1° or more, 3° or more, 5° or more, or even 7° or more. The angle may be about 15° or less, 13° or less, 11° or less, or even 9° or less. The haptics may be planar and/or step-vaulted.

The shape, size, orientation, and/or number of the haptics may depend on the location within the eye where the prosthetic is to be located.

Examples of suitable haptics are disclosed in U.S. Pat. Nos. 4,634,442; 5,192,319; 6,106,553; 6,228,115; and 7,455,691, which are incorporated herein by reference in their entirety for all purposes.

The ophthalmic prosthetic may include a fiber portion or may be free of a fiber portion. The fiber portion may function to increase the mechanical strength (e.g., tearing strength) of the ophthalmic prosthetic. The fiber portion may be included in the ophthalmic prosthetic where suturing the ophthalmic prosthetic is desired (e.g., suturing of haptics). The fiber portion may allow the ophthalmic prosthetic to withstand tearing or cheese-wiring imposed by suturing. An ophthalmic prosthetic that is free of a fiber portion may be suitable for suturing, however looser sutures may be necessary to prevent tearing or cheese-wiring. Cheese-wiring, as referred to herein, may mean the cutting or deformation the ophthalmic prosthetic caused by the tension of sutures.

The fiber portion may be fabricated from a polymer meshwork. The polymer may include polyester, expanded polytetrafluoroethylene, polymethylmethacrylate, polycarbonate, polyvinylidene fluoride, polyvinyl chloride, polypropylene, polyethylene, polystyrene, polyether ether ketone, polysulfone, polyimide, prolene, hydrophilic acrylic, hydrophobic acrylic, hydrogel, silicone, the like, or any combination thereof.

The fiber portion may be fabricated by material addition and/or material removal, as taught herein.

The fiber portion may be provided as one or more layers on and/or within the ophthalmic prosthetic. The fiber portion may be located on an anterior surface and/or posterior surface of the ophthalmic prosthetic. The ophthalmic prosthetic may be molded around the fiber portion. The fiber portion may be laminated with layers of the ophthalmic prosthetic. The fiber portion may be adhered to the ophthalmic prosthetic.

Fabrication

The ophthalmic prosthetic may be fabricated by material removal and/or material addition. Material removal may include milling, lathing, grinding, etching, or any combination thereof. Material addition may include molding, 3D printing, thin film deposition, spraying, brushing, rolling, swabbing, or any combination thereof.

Material removal and/or material addition may be employed to realize the final dimensions of an ophthalmic prosthetic, fabricate surface modifications, or both.

Milling and/or lathing may be performed with tooling. Examples of suitable tooling employed with lathing processes may include, but is not limited to, turning bits, facing bits, chamfering bits, boring bits, concave bits, convex bits, cutoff bits, the like, or any combination thereof. Examples of suitable tooling employed with milling processes may include, but is not limited to, square bits, ball bits, tapered bits, engraving bits, the like, or any combination thereof.

The tooling may have a surface roughness that is transferred to a surface upon its interaction with the tooling. The surface roughness of the tooling may be deliberately selected to provide the desired surface roughness. The surface roughness may be produced by deflection of the tooling and/or surface. The surface roughness may be produced by geometric error or the milling or lathing equipment.

Milling and/or lathing may be performed with micro-tooling. Micro-tooling may have a diameter of about 40 μm or more, 60 μm or more, 70 μm or more, or even 80 μm or more. Micro-tooling may have a diameter of about 160 μm or less, 140 μm or less, 120 μm or less, or even 100 μm or less.

Grinding may be performed with an abrasive substrate, abrasive compound, or both. The abrasive substrate may be a surface coated with abrasive particles. The abrasive particles may be adhered to the surface. The abrasive substrate may be a material with a roughened surface. The abrasive substrate may be ANSI (American National Standards Institute) rated 60 grit or more, 80 grit or more, 100 grit or more, 150 grit or more, or even 220 grit or more. The abrasive substrate may be ANSI rated 1200 grit or less, 800 grit or less, 500 grit or less, 360 grit or less, or even 280 grit or less. The abrasive compound may comprise a suspension of abrasive particles in a liquid medium. The liquid may be a paste. The abrasive particles may be about 5 $\mu m$ or more, 10 $\mu m$ or more, 50 $\mu m$ or more, or even 100 $\mu m$ or more in their largest dimension. The abrasive particles may be about 600 $\mu m$ or less, 500 $\mu m$ or less, 400 $\mu m$ or less, or even 300 $\mu m$ or less in their largest dimension.

Etching may be performed by exposing one or more surfaces to an acidic (e.g., hydrofluoric acid, sulfuric acid, or nitric acid) or basic (e.g., potassium hydroxide, sodium hydroxide, or tetramethylammonium hydroxide) solution. This may otherwise be referred to as chemical etching. The acid or base may be present in an aqueous solution. Chemical etching may remove material. Chemical etching may remove material from a surface by influencing the scission of polymer chains. Chemical reactions of the surface may be ceased by quenching the acidic or basic solution with a neutralizing solution. The etching may give rise to surface roughness, as described herein.

The depth of chemical etching (i.e., depth below a mean plane of a pre-etched/engraved surface, as disclosed herein) may be modulated by the exposure time, pH, acid/base concentration, temperature, or any combination thereof. The depth may be about 0.001 $\mu m$ or more, 0.01 $\mu m$ or more, 0.1 $\mu m$ or more, or even 1 $\mu m$ or more. The depth may be about 50 $\mu m$ or less, 40 $\mu m$ or less, 30 $\mu m$ or less, 20 $\mu m$ or less, or even 10 $\mu m$ or less.

Etching may be performed with radiation. This may otherwise be referred to as laser etching. A laser may be employed which emits light radiation of a wavelength between about 3 $\mu m$ and about 50 $\mu m$ (i.e., mid- to far-infrared). Laser etching may sublimate polymer from the surface by the generation of heat upon the surface.

The depth of laser etching (i.e., depth below a mean plane of a pre-etched/engraved surface, as disclosed herein) may be modulated by the exposure time, wavelength, intensity, or any combination thereof. The depth may be about 0.001 $\mu m$ or more, 0.01 $\mu m$ or more, 0.1 $\mu m$ or more, or even 1 $\mu m$ or more. The depth may be about 50 $\mu m$ or less, 40 $\mu m$ or less, 30 $\mu m$ or less, 20 $\mu m$ or less, or even 10 $\mu m$ or less.

Molding may include injection molding, co-injection molding, and/or overmolding. Co-injection molding and/or overmolding may be particularly advantageous where the annular portion is a discrete structure from the material of the ophthalmic prosthetic. Co-injection molding and/or overmolding may be particularly advantageous where a fiber portion, as disclosed herein, is employed.

3D printing ("additive manufacturing") may involve the deposition of material in a plurality of layers to sequentially build up the ophthalmic prosthetic. Deposition may be skipped in regions of the ophthalmic prosthetic to define grooves and/or apply material in discrete regions to define ridges. Material may be deposed as one or more continuous lengths of extrudate, jetted droplets, or both. Material may or may not be deposed onto or into a mold. The mold may include a negative impression of surface modifications (e.g., surface topography) thereon. During deposition of material, the material may be shaped by the negative impression. Upon hardening and/or curing of the material, the negative impression may be fixed in the material. Material may be removed from the 3D printed ophthalmic prosthetic to achieve desired dimensions, and/or surface roughness.

The ophthalmic prosthetic may be fabricated to include passageways between the anterior and posterior surfaces thereof. The passageways may function to facilitate the flow of fluids and nutrients through the ophthalmic implant. The passageways may be uniform or non-uniform. The passageways may be configured to prevent light from passing through the passageways and striking the retina. By way of example, the passageways may be oriented in a direction in which light cannot pass from the anterior surface to the posterior surface of the ophthalmic prosthetic. By way of another example, the passageways may include internal angular turns or bends.

Passageways may be fabricated by skipping regions during material addition (e.g., 3D printing). Individual passageways may be contiguously angularly oriented during the deposition of one or more layers. Individual passageways may be oriented at two or more different angles as they extend from the anterior surface to the posterior surface of the ophthalmic prosthetic.

Thin film deposition may include physical vapor deposition, chemical vapor deposition, or both. Thin film deposition may provide a layer having a thickness of about 1 nm or more, 5 nm or more, 10 nm or more, or even 20 nm or more. Thin film deposition may provide a layer having a thickness of about 500 nm or less, 300 nm or less, 100 nm or less, or even 50 nm or less.

Method

The method may comprise one or more of the following steps. Some of the steps may be duplicated, removed, rearranged relative to other steps, combined into one or more steps, separated into two or more steps, or a combination thereof.

The present disclosure provides for a method for correcting negative and positive dysphotopsia for a person in need of correction of negative and positive dysphotopsia caused by a gap between an iris and intraocular lens or at risk for developing such a symptom. The method may comprise forming an incision in a cornea, inserting an ophthalmic prosthetic into an eye through the incision, and locating the ophthalmic prosthetic between the iris and the intraocular lens. The ophthalmic prosthetic or at least a sector thereof may be located the nasal hemisphere of an eye.

The method further comprises fixating the ophthalmic prosthetic to one or more structures of the eye. The ophthalmic prosthetic is passively fixated within a capsular bag or a ciliary sulcus. Passively fixated, as referred to herein, may mean engaged with a ciliary sulcus, ciliary body, iris, intraocular lens, or any combination thereof. An anterior surface of the ophthalmic prosthetic may be engaged with the ciliary sulcus, ciliary body, iris, intraocular lens, or any combination thereof. A posterior surface of the ophthalmic prosthetic may be engaged with the ciliary sulcus, ciliary body, iris, intraocular lens, or any combination thereof. An outer perimeter of the ophthalmic prosthetic may be engaged with the ciliary sulcus, ciliary body, iris, intraocular lens, internal eye wall, or any combination thereof.

The ophthalmic prosthetic may be fixated via haptics, sutures, or both. The haptics may be engaged with the ciliary sulcus, ciliary body, iris, intraocular lens, or any combination thereof. The sutures may be coupled to the ciliary sulcus, ciliary body, iris, intraocular lens, or any combination thereof.

The incision may be no greater than 8 mm in the largest dimension of the incision, more preferably 6 mm, or even more preferably 3 mm. The largest dimension may be a diameter of a circle, a length along a major axis of an ellipse, a length between diametrically opposed corners of a regular polygon, or a length between two most distanced corners of an irregular polygon.

The method may further include rolling the ophthalmic prosthetic into a roll having a major diameter no greater than 3 mm.

DETAILED DESCRIPTION OF THE DRAWINGS

FIG. 1 is a plan view of an eye 10. The eye 10 resides in an eye socket in the skull. The eye 10 includes an annular portion of pigmented tissue known as the iris 14. The iris 14 includes smooth muscle for controlling and regulating the size of a pupil 16 defined by the iris 14, the pupil 16 being an opening in the iris 14. The eye 10 includes a cornea 12 that covers and protects both the iris 14 and pupil 16.

Figure 2:
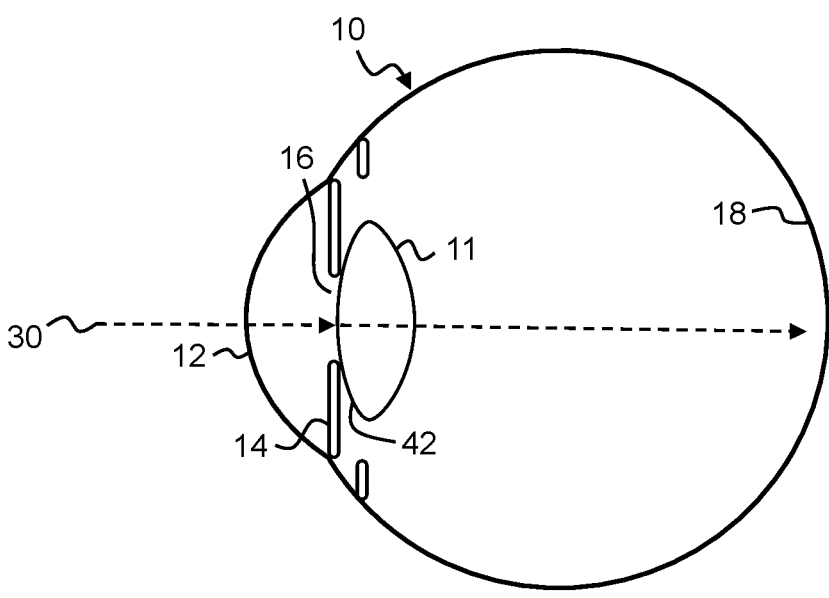
FIG. 2 is a bi-sectional view of the eye illustrated in FIG. 1.

FIG. 2 is a bi-sectional view of the eye 10 illustrated in FIG. 1. The eye 10 includes a natural lens 11 located therein. The natural lens 11 is in contact with the iris 14. The iris 14 drapes across and contours the convex anterior surface 42 of the natural lens 11. A light ray 30 enters the eye 10 through the cornea 12, passes through the pupil 16, and interacts with the intraocular lens 13. The light ray 30 is refracted toward the posterior portion of the retina.

Figure 3A:
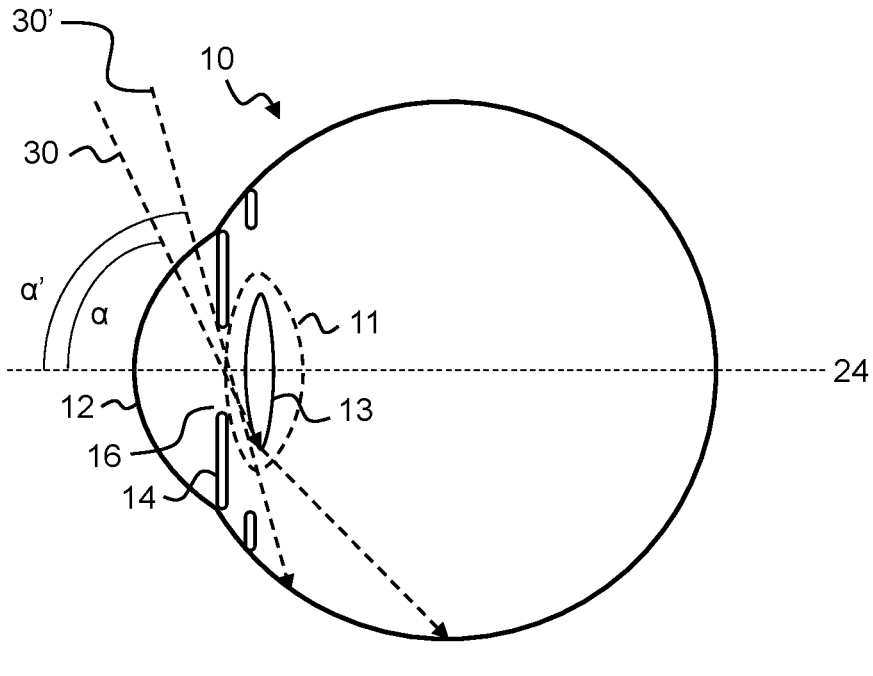
FIG. 3A is a bi-sectional view of the eye illustrated in FIG. 1.
Figure 3B:
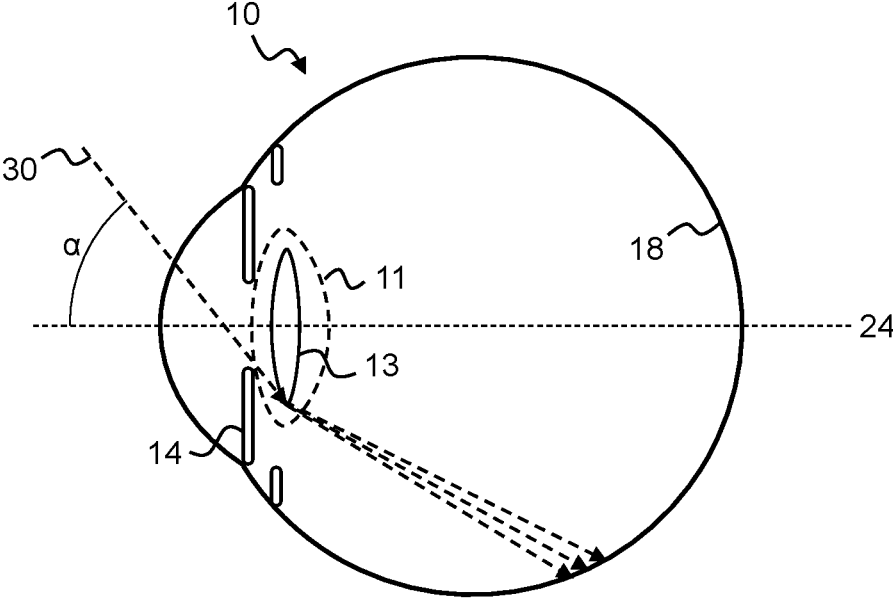
FIG. 3B is a bi-sectional view of the eye illustrated in FIG. 1.

FIG. 3A and FIG. 3B are bi-sectional views of the eye 10 illustrated in FIG. 1. The eye 10 includes an artificially fabricated intraocular implant lens 13 located therein. The natural lens 11, as shown in FIG. 2, is illustrated in dashed lines to clearly show the dimensional and positional difference between the natural lens 11 and the implanted intraocular lens 13. The intraocular implant lens 13 is thinner than the natural lens 11 and thus, the iris 14 does not contour or otherwise contact the intraocular implant lens 13. Due to positioning of the intraocular implant lens 13, a gap is located between the intraocular implant lens 13 and the iris 14.

As shown in FIG. 3A, light rays 30, 30' entering the eye 10 at an angle α, α' to the optical axis 24. The light ray 30 is refracted by the edge of the lens and directed more posteriorly. The adjacent light ray 30' misses the edge of the lens and passes through the gap between the intraocular lens 13 and the iris 14, allowing it to pass un-refracted peripheral to the edge of the intraocular lens. The space between where the adjacent light rays 30 and 30' strike the retina represents the illumination gap. FIG. 3A. This illumination gap gives rise to negative dysphotopsia perceived by the patient. Blocking access of light to the gap prevents this phenomenon.

As shown in FIG. 3B, a light ray 30 enters the eye 10 at an angle α to the optical axis 24 and strikes the anterior edge of the intraocular implant lens 13. The light ray 30 is diffracted and/or dispersed resulting in positive dysphotopsia. Blocking access of light to the intraocular implant lens 13 edge prevents this phenomenon.

Figure 4A:
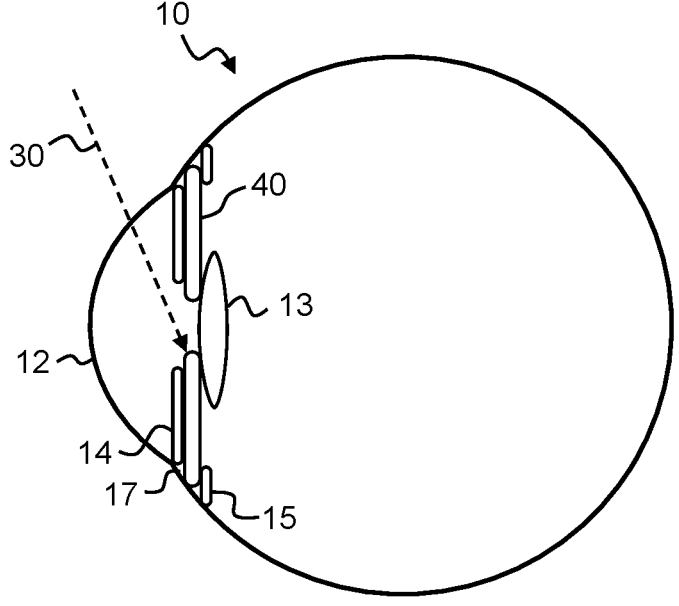
FIG. 4A is a bi-sectional view of the eye illustrated in FIG. 1.
Figure 4B:
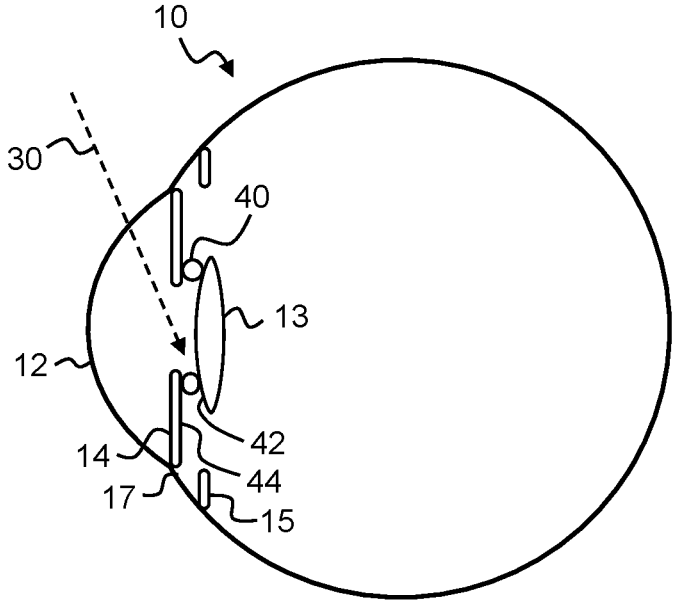
FIG. 4B is a bi-sectional view of an eye such as that illustrated in FIG. 1.

FIG. 4A and FIG. 4B are bi-sectional views of the eye 10 illustrated in FIG. 1. The eye 10 includes an artificially fabricated intraocular implant lens 13 located therein. Due to positioning of the intraocular implant lens 13, a gap is located between the intraocular implant lens 13 and the iris 14. The eye 10 includes an ophthalmic prosthetic 40 according to the present disclosure. The ophthalmic prosthetic 40 is located within the gap between the intraocular implant lens 13 and the iris 14. The ophthalmic prosthetic 40 of FIG.

4A is fixated in the eye 10, at least in part, due to its engagement with the ciliary sulcus 17 located between the iris 14 and the ciliary body 15. The ophthalmic prosthetic 40 of FIG. 4B is fixated in the eye 10, at least in part, due to its engagement between the implanted intraocular lens 13 and the iris 14. Light rays 30 entering the eye 10 are blocked from travelling through the gap by the ophthalmic prosthetic 40.

The ophthalmic prosthetic 40 may extend laterally toward the internal eye 10 wall, as shown in FIG. 4A, thereby blocking light rays. The ophthalmic prosthetic 40 may fill an anterior-posterior axial space between the anterior surface 42 of the ophthalmic prosthetic 40 and the posterior surface 44 of the iris 14, as shown in FIG. 4A and FIG. 4B. It is contemplated by the present disclosure that the ophthalmic prosthetic 40 illustrated in FIG. 4A may extend laterally toward the internal eye 10 wall but not fill an anterior-posterior axial space between the anterior surface of the ophthalmic prosthetic 40 and the posterior surface of the iris 14.

Figure 5:
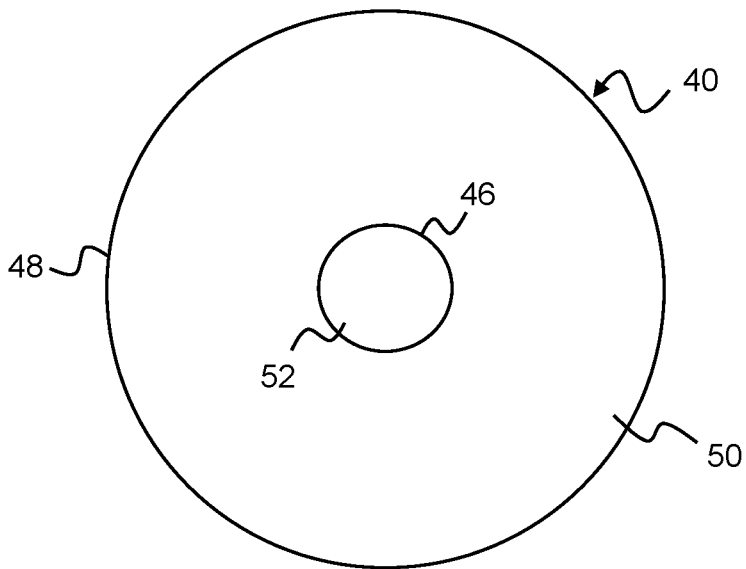
FIG. 5 is a plan view of an ophthalmic prosthetic according to the present disclosure.

FIG. 5 is a plan view of an ophthalmic prosthetic 40 according to the present disclosure. The ophthalmic prosthetic 40 has a generally annular profile, contiguous over 360°, defined by an outer perimeter 48 of a peripheral light-blocking implant member 50. The ophthalmic prosthetic 40 comprises a peripheral light-blocking implant member 50, which may be opaque, partially opaque, translucent, and/or polarized. The peripheral light-blocking implant member 50, when implanted into an eye 10, such as that illustrated in FIGS. 4A and 4B, blocks light rays 30 from travelling through the gap between the intraocular lens 13 and the iris 14 or striking an edge of the intraocular implant lens 13. The ophthalmic prosthetic 40 comprises an interior light transmitting portion 52, defined by an inner perimeter 46 of the peripheral light-blocking implant member 50, through which light rays 30 travel and into the eye 10.

Figure 6:
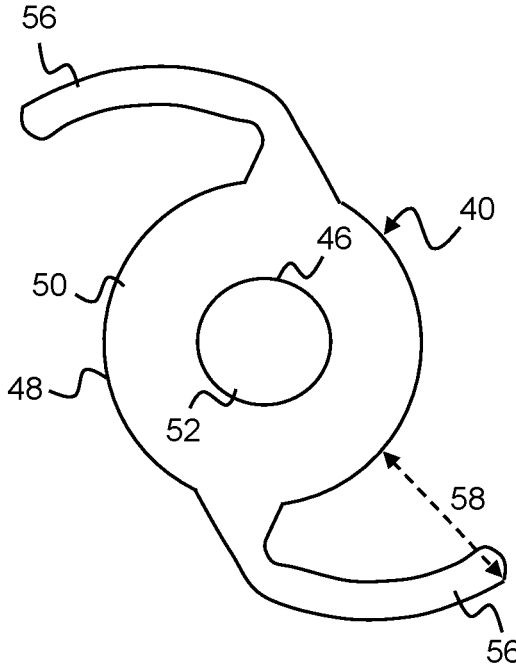
FIG. 6 is a plan view of an ophthalmic prosthetic according to the present disclosure.

FIG. 6 and FIG. 7 are plan views of an ophthalmic prosthetic 40 according to the present disclosure. The ophthalmic prosthetic 40 illustrated in FIG. 6 has a generally annular profile, contiguous over 360°, defined by an outer perimeter 48 of a peripheral light-blocking implant member 50. The ophthalmic prosthetic 40 illustrated in FIG. 7 has a generally annular sector profile contiguous over 180°. The ophthalmic prosthetic 40 comprises a peripheral light-blocking implant member 50, which may be opaque, partially opaque, translucent, and/or polarized. The peripheral light-blocking implant member 50, when implanted into an eye 10, such as that illustrated in FIG. 4A and FIG. 4B, blocks light rays 30 from travelling through the gap between the intraocular lens 13 and the iris 14 or striking an edge of the intraocular implant lens 13. The ophthalmic prosthetic 40 comprises an interior light transmitting portion 52, defined by an inner perimeter 46 of the peripheral light-blocking implant member 50, through which light rays 30 travel and into the eye 10. The ophthalmic prosthetic 40 comprises two J-shaped haptics 56 extending a length 58 radially from the outer perimeter 48 of the ophthalmic prosthetic 40. The haptics 56 extend from opposing sides of the outer perimeter 48. The haptics 56 include one end coupled to the outer perimeter 48 and end that is free.

Figure 8:
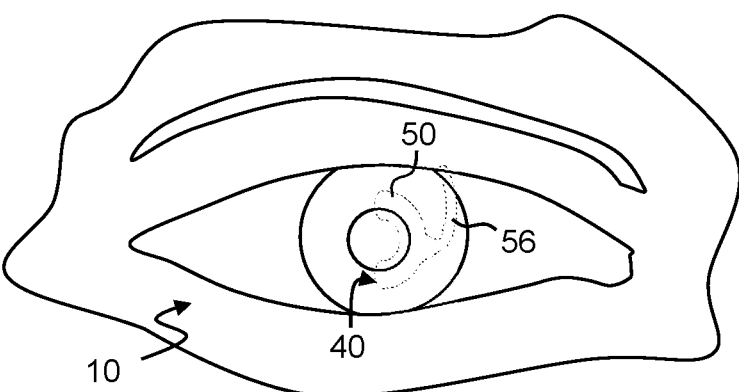
FIG. 8 is a plan view of an eye.

FIG. 8 is a plan view of an eye 10. The eye 10 includes an ophthalmic prosthetic 40 according to the present disclosure implanted therein. The ophthalmic prosthetic 40 has a generally annular sector profile contiguous over 180°, as illustrated in FIG. 7. The ophthalmic prosthetic 40 comprises a peripheral light-blocking implant member 50 located in the nasal hemisphere of the eye 10. The ophthalmic prosthetic 40 comprises a J-shaped haptic 56 extending therefrom. The haptic 56 is located within the ciliary sulcus 17, as shown in FIG. 4A and FIG. 4B.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The terms "generally" or "substantially" to describe angular measurements may mean about +/–10° or less, about +/–5° or less, or even about +/–1° or less. The terms "generally" or "substantially" to describe angular measurements may mean about +/–0.01° or greater, about +/–0.1° or greater, or even about +/–0.5° or greater. The terms "generally" or "substantially" to describe linear measurements, percentages, or ratios may mean about +/–10% or less, about +/–5% or less, or even about +/–1% or less. The terms "generally" or "substantially" to describe linear measurements, percentages, or ratios may mean about +/–0.01% or greater, about +/–0.1% or greater, or even about +/–0.5% or greater.

Unless otherwise stated, any numerical values recited herein include all values from the lower value to the upper value in increments of one unit provided that there is a separation of at least 2 units between any lower value and any higher value. As an example, if it is stated that the amount of a component, a property, or a value of a process variable such as, for example, temperature, pressure, time, and the like is, for example, from 1 to 90, from 20 to 80, or from 30 to 70, it is intended that intermediate range values such as (for example, 15 to 85, 22 to 68, 43 to 51, 30 to 32 etc.) are within the teachings of this specification. Likewise, individual intermediate values are also within the present teachings. For values which are less than one, one unit is considered to be 0.0001, 0.001, 0.01, or 0.1 as appropriate. These are only examples of what is specifically intended and all possible combinations of numerical values between the lowest value and the highest value enumerated are to be considered to be expressly stated in this application in a similar manner. Unless otherwise stated, all ranges include both endpoints and all numbers between the endpoints.

As can be seen, the teaching of amounts expressed as "parts by weight" herein also contemplates the same ranges expressed in terms of percent by weight. Thus, an expression of a range in terms of "at least 'x' parts by weight of the resulting composition" also contemplates a teaching of ranges of the same recited amount of "x" in percent by weight of the resulting composition."

The term "consisting essentially of" to describe a combination shall include the elements, ingredients, components, or steps identified, and such other elements ingredients, components or steps that do not materially affect the basic and novel characteristics of the combination. The use of the terms "comprising" or "including" to describe combinations of elements, ingredients, components, or steps herein also contemplates embodiments that consist essentially of the elements, ingredients, components, or steps.

Plural elements, ingredients, components, or steps can be provided by a single integrated element, ingredient, component, or step. Alternatively, a single integrated element, ingredient, component, or step might be divided into separate plural elements, ingredients, components, or steps. The disclosure of "a" or "one" to describe an element, ingredient, component, or step is not intended to foreclose additional elements, ingredients, components, or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

REFERENCE NUMERALS

10 Eye
11 Natural lens
12 Cornea
13 Intraocular implant lens
14 Iris
15 Ciliary body
16 Pupil
17 Ciliary sulcus
18 Retina
24 Optical axis
30 Light ray
40 Ophthalmic prosthetic
42 Anterior surface
44 Posterior surface
46 Inner perimeter
48 Outer perimeter
50 Peripheral light-blocking implant member
52 Interior light transmitting portion
56 Haptic
58 Length

What is claimed is:

1. A method for correcting negative and positive dysphotopsia for a person in need of correction of or at risk for positive and negative dysphotopsia caused by light passing between an iris or ciliary body and an intraocular lens of an eye, the method comprising:

forming an incision in a cornea, inserting an ophthalmic prosthetic, which includes an annular body or an annular segment, into the eye, between the iris and the intraocular lens, through the incision, and locating the annular body or annular segment either within a capsular bag or within a ciliary sulcus, to completely fill an axial gap and/or substantially fill a radial gap between the iris and the intraocular lens and block the light, which travels through the pupil and tangentially to the intraocular lens, from striking or bypassing a circumferential edge of the intraocular lens and striking an anterior retina, the axial and/or radial gap being present prior to the inserting of the ophthalmic prosthetic into the eye, and wherein the ophthalmic prosthetic has anterior and posterior surfaces that are both located anteriorly of the intraocular lens.

2. The method according to claim 1, wherein the ophthalmic prosthetic or at least a sector thereof is located in a nasal hemisphere of the eye, a temporal hemisphere of the eye, or both.

3. The method according to claim 1, wherein the method further comprises fixating the ophthalmic prosthetic to one or more structures of the eye.

4. The method according to claim 3, wherein the ophthalmic prosthetic is passively fixated within the capsular bag or the ciliary sulcus.

5. The method according to claim 3 wherein the ophthalmic prosthetic is fixated via a periphery of the ophthalmic prosthetic, haptics, sutures, or any combination thereof.

6. The method according to claim 1, wherein the method further includes rolling the ophthalmic prosthetic into a roll having a major diameter no greater than 3 mm.

7. The method according to claim 1, wherein the annular body or annular segment of the ophthalmic prosthetic has an outer diameter of between 9 mm and 15 mm such that the radial gap is filled in a coronal plane of the eye.

8. The method according to claim 7, wherein the ophthalmic prosthetic has a thickness of about 0.05 mm to about 1.2 mm such that the axial gap is filled.

9. The method according to claim 1, wherein the annular body or annular segment is opaque, partially opaque, translucent, polarized, froster, or any combination thereof.

10. A method for correcting negative and positive dysphotopsia for a person in need of correction of or at risk for positive and negative dysphotopsia caused by light passing between an iris or ciliary body and an intraocular lens of an eye, the method comprising:

forming an incision in a cornea, inserting an ophthalmic prosthetic, which includes an annular body or an annular segment, into the eye, between the iris and the intraocular lens, through the incision, and locating the annular body or annular segment either within a capsular bag or within a ciliary sulcus, to completely fill an axial gap and/or substantially fill a radial gap between the iris and the intraocular lens and block the light, which travels through the pupil and tangentially to the intraocular lens, from striking or bypassing a circumferential edge of the intraocular lens and striking an anterior retina, the axial and/or radial gap being present prior to the inserting of the ophthalmic prosthetic into the eye; and wherein the annular body or annular segment of the ophthalmic prosthetic has an outer diameter that fills the radial gap in a coronal plane of the eye and/or the ophthalmic prosthetic has a thickness of about 0.05 mm to about 1.2 mm such that the axial gap is filled; and wherein the ophthalmic prosthetic has anterior and posterior surfaces that are both located anteriorly of the intraocular lens.

11. The method according to claim 10, wherein the annular body or annular segment is opaque, partially opaque, translucent, polarized, frosted, or any combination thereof.

* * * * *